United States Patent [19]
Yasushi et al.

[11] Patent Number: 6,084,516
[45] Date of Patent: Jul. 4, 2000

[54] AUDIO APPARATUS

[75] Inventors: Mitsuo Yasushi; Masatoshi Yanagidaira; Jun Cheng; Kayoko Takashima; Hiroshi Satoh; Kazuyuki Uchiyama; Koji Watanabe, all of Tokyo, Japan

[73] Assignee: Pioneer Electronic Corporation, Tokyo, Japan

[21] Appl. No.: 09/199,373

[22] Filed: Nov. 25, 1998

[30] Foreign Application Priority Data

Feb. 6, 1998 [JP] Japan .................................. 10-041056

[51] Int. Cl.[7] .................................................. G08B 23/00
[52] U.S. Cl. ..................................... 340/573.1; 340/691.8; 340/692; 340/825.49; 381/23.1; 381/81
[58] Field of Search ............................. 340/573.1, 691.8, 340/692, 666, 825.49, 825.5; 455/404, 527; 381/23.1, 312, 315, 81, 85

[56] References Cited

U.S. PATENT DOCUMENTS

| | | | |
|---|---|---|---|
| 4,107,464 | 8/1978 | Lynch et al. | 340/692 X |
| 4,389,639 | 6/1983 | Torii et al. | 340/692 X |
| 5,131,048 | 7/1992 | Farenelli et al. | 381/81 |
| 5,153,584 | 10/1992 | Engira | 340/573.1 X |
| 5,905,436 | 5/1999 | Dwight et al. | 340/573.1 |
| 5,917,414 | 6/1999 | Oppelt et al. | 340/573.1 |
| 5,917,425 | 6/1999 | Crimmins et al. | 340/573.1 X |

FOREIGN PATENT DOCUMENTS

| | | |
|---|---|---|
| 102877 | 4/1994 | Japan . |
| 22495 | 1/1997 | Japan . |
| 19782 | 9/1994 | WIPO . |

*Primary Examiner*—Thomas Mullen
*Attorney, Agent, or Firm*—Sughrue, Mion, Zinn, Macpeak & Seas, PLLC

[57] ABSTRACT

The living condition of a resident is prehended by a sensor disposed in a room. Identification information and vital information transmitted from a portable transreceiver carried by the resident are monitored. An audio signal favored by the resident is sequentially reproduced while the level is adjusted in accordance with the current living condition and physical condition of the resident.

7 Claims, 2 Drawing Sheets

FIG. 2

AUDIO APPARATUS

BACKGROUND OF THE INVENTION

The present invention relates to an audio apparatus which supplies an optimum audio signal to a resident (including an aged person, a child, and a handicapped person), and particularly to an audio apparatus which makes a notification when an abnormality is detected in the body of the user.

Conventionally, a so-called stereo system is used as a home audio reproducing apparatus. In such a system, a resident sets a favorite recording medium such as a CD or a cassette tape to a playing apparatus such as a CD player or a cassette tape player connected to an amplifier, and a performance is then conducted, so that the resident listens to music or the like through loudspeakers connected to the amplifier. Such a stereo system is usually aimed at a healthy person who can enjoy a stereo performance. As required, the subject operates a remote controller or a volume knob disposed on the amplifier to conduct selection of a favorite music piece, adjustment of volume, or the like, so that the subject can enjoy music.

On the other hand, the approach of an aged society is impending. In homes, the rate of aged persons requiring home nursing is rapidly increasing. In communities, it is requested to immediately expand facilities for social welfare for aged persons.

Under such circumstances, in a home or a facility where healthy persons live together with aged persons, handicapped persons, or the like, each person goes about his daily routing according to his own leisure. Even in such a case, it is preferable that the persons can commonly enjoy music and sometimes individually enjoy music while the volume and the like are set in accordance with their respective conveniences.

Generally, the physical condition of an aged person daily changes to a larger degree than a healthy person. Therefore, aged persons are required to always monitor their own physical condition by themselves or by means of an emergency medical system or the like. An example of an emergency medical system for residents at home, particularly, aged persons is disclosed in, for example, the Unexamined Japanese Patent Application Publication No. Hei 9-22495. In the disclosed system, a resident carries on the arm a life wrist band which can measure the pulse and the heartbeat and which has an emergency button, and plural passive sensors, each having a human body sensor which monitors motion are previously disposed at plural places in the house. During the resident's daily activities, signals due to the pulse, the heartbeat, the motion of the resident, and the like are monitored by a monitor terminal via the life wrist band and the passive sensors. When an abnormality occurs, the occurrence is automatically rapidly communicating via a telephone line to a medical institution, a physician in charge, etc. When the resident senses an abnormality, the resident can press the emergency button to send an emergency signal. This signal is received by the monitor terminal, so that the abnormality is rapidly communication to an emergency facility and medical data are transferred.

Such an emergency medical system is configured so that, when the state of the resident is judged to be abnormal or when the resident feels ill, warning is given to a medical institution, a physician in charge, an emergency facility, and the like. The system is not considered to be applied to a system of another kind. When an aged person is to enjoy music by means of an audio apparatus, therefore, such a system must be separately disposed in addition to the audio apparatus. This causes the whole system to be complicated, and the cost to be increased.

Even when these systems are jointly used, an aged person cannot individually enjoy music at ease because, when the attention of a person is focused on the music, the person pays no attention to the monitoring of his own physical condition. Furthermore, the physical condition of an aged person is easily affected by the external environment such as date, a time, and weather. In some cases, when the person listens to disliked music which is selected by another resident, the pulse, the heartbeat, the blood pressure, the brain waves, the respiration rate, the body temperature, the perspiration of the resident, and the like may be caused to be largely varied.

The Unexamined Japanese Patent Application Publication No. Hei 6-102877 discloses an audio constituting apparatus which detects input information from the external environment such as physiological data and external environment data, and produces a predetermined audio signal. The apparatus is configured so that a change of the state of the external environment received via input means such as a sensor is converted into a signal and then output; data extracting means analyzes the output signal to extract data such as the pitch and the volume; tone generator controlling means outputs tone generator control data obtained by changing attributes such as the pitch, the volume, the sound waveform functioning as the tone color, and the envelope in accordance with determined attributes on the basis of tone generator data extracted by the data extracting means; and the output signal is converted and then output as a sound via sound outputting means, so that the output sound is constituted to be completely different from the original sound. Therefore, the listener and the listening environment mutually affect each other, and the sound reproduction which is rich in contingency, unexpectedness, and interactive facility is enabled.

In such a configured audio constituting apparatus, the apparatus itself conducts sound reproduction according to preset attributes and in accordance with the external environment, and irrespective of the physical condition of an aged person. As a result, the listener cannot conduct sound reproduction corresponding to the physical condition, and hence cannot enjoy favorite audio signals (music and sounds of the natural world) in accordance with physical condition and at ease. Even when the listener who is an aged person is at any place in a room, furthermore, an audio signal of a level which is irrespective of physical condition is output. Therefore, the audio signal is sometimes hard to hear, and the volume is too high, whereby the listener often feels uncomfortable.

SUMMARY OF THE INVENTION

The invention has been conducted in view of the above-discussed problems. It is an object of the invention to provide an audio apparatus which can be used comfortably and at ease even when a resident such as an aged person is in any room in a residence or building ordinarily visited.

The invention set forth in aspect 1 is configured by an audio apparatus comprising: vital information detecting means for detecting vital information of a resident; a database which is configured by information based on the vital information, and in which at least vital information in a normal state of the resident is accumulated; audio signal generating means for generating a normal audio signal and a warning audio signal; comparing means for comparing the vital information in a normal state which is accumulated in the database, with the vital information detected by the vital information detecting means; selecting means for, if vital information detected on the basis of a result of the comparison of the comparing means is information in a normal state, selecting the normal audio signal of the audio signal generating means, and, if the vital information is not information in a normal state, selecting the warning audio signal; and audio signal producing means for producing the selected audio signal to the resident.

The invention set forth in aspect 2 is configured by an audio apparatus comprising: a position detection sensor which produces a detection signal corresponding to a position of a resident in a room; audio signal generating means for generating an audio signal; loudspeakers which are respectively disposed at predetermined places in the room, and which output the audio signal from the audio signal generating means; and level setting means for, on the basis of the detection signal from the position detection sensor, setting the audio signal supplied to the loudspeakers to a predetermined level.

The invention set forth in aspect 3 is configured by an audio apparatus comprising: identification signal producing means, carried by a resident, for producing an identification signal for identifying the resident; common audio signal generating means for generating a common audio signal; common audio signal producing means for producing the common audio signal in a first room; individual audio signal generating means for generating a plurality of individual audio signals corresponding to the identification signal of the resident; identification signal receiving means, which may be disposed in a second room, for receiving the identification signal from the identification signal producing means; selecting means for, from the individual audio signal generating means, selecting an individual audio signal corresponding to the identification signal received by the identification signal receiving means; and individual audio signal producing means for producing the selected individual audio signal in the second room.

The invention set forth in aspect 4 is configured so that, in the audio apparatus of aspect 1, the vital information detecting means is attached to a hearing aid.

The invention set forth in aspect 5 is configured so that, in the audio apparatus of aspect 3, the identification signal producing means is attached to a hearing aid.

The invention set forth in aspect 6 is configured so that, in the audio apparatus of aspect 1, together with vital information, external data such as data relating to a date, a time, and weather when the vital information is detected are accumulated in the database, and the vital information in a normal state of the resident is set in accordance with these data.

The invention set forth in aspect 7 is configured so that, in the audio apparatus of aspect 2, the position detection sensor comprises light emitting means carried by the resident, and light receiving means, respectively disposed at predetermined places in the room, for receiving light from the light emitting means.

In the invention configured as described above, the vital information detecting means detects vital information of a resident; at least vital information in a normal state of the resident is accumulated in the database; the comparing means compares the vital information in a normal state which is accumulated in the database, with the vital information detected by the vital information detecting means; if the detected vital information is information in a normal state, the normal audio signal of the audio signal generating means is selected, and, if the vital information is not information in a normal state, the warning audio signal is selected; the audio signal producing means produces the selected audio signal for the resident. Even when the attention of the resident is focused on the normal audio signal, therefore, the signal is switched to the warning audio signal in the case of emergency. Consequently, even when a resident such as an aged person is in any room ordinarily visited, the person can enjoy music comfortably and at ease.

Furthermore, the position detection sensor detects the position of a resident in a room, and produces a detection signal corresponding to the detected position; and, on the basis of the detection signal, the level setting means sets the audio signal generated by the audio signal generating means, to a predetermined level, and supplies the audio signal to the loudspeakers which are respectively disposed at predetermined places in the room. Even when a resident is at any position, therefore, the resident can enjoy music at the volume and a level of sound quality which are suitable to the resident.

When a resident moves from the first room (a common living space such as a living room or a reception room) where the common audio signal is produced by the common audio signal producing means, to the second room (a private space such as a toilet room, a bathroom, or a private room), the identification signal receiving means disposed in the second room receives the identification signal from the identification signal producing means carried by the resident, and the selecting means selects an individual audio signal corresponding to the identification signal. Therefore, the resident can enjoy the selected audio signal which is selected for the resident.

DETAILED DESCRIPTION OF THE PREFERRED EMBODIMENTS

Next, preferred embodiments of the invention will be described with reference to the figures.

Figure 1:
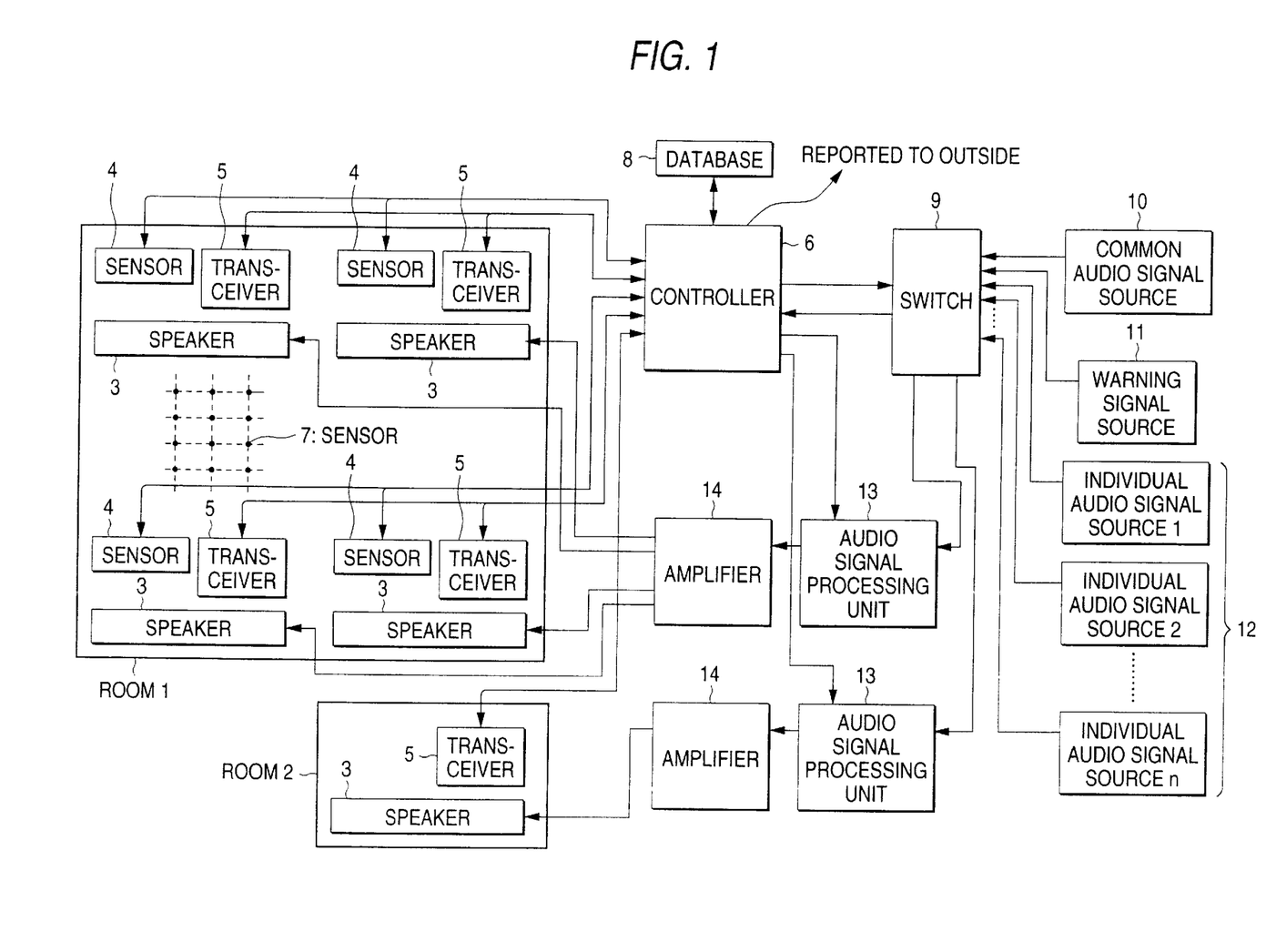
FIG. 1 is a system block diagram showing a state where an audio apparatus of an embodiment of the invention is disposed in each room of a house.

FIG. 1 is a system block diagram showing a state where an audio apparatus of an embodiment of the invention is disposed in each room of a house. In the embodiment, it is assumed that the family includes a person who might need assistance, for example, an aged person who has difficulty in hearing, or a person who requires physical care. Referring to the figure, a room 1 is a common living space where plural persons exist in turns, such as a living room or a reception room. A room 2 is a space which is to be occupied by a single person, such as a toilet room, a bathroom, or a private room. In the figure, each of the rooms 1 and 2 is indicated as a single room. Actually, each of the rooms may be configured by plural rooms.

In the room 1, plural loudspeakers 3 are disposed at predetermined places (for example, the four corners), respectively. Plural sensors 4 are disposed in proximity to the loudspeakers 3 of the room 1 so as to correspond thereto, respectively. The sensors 4 are infrared receivers for detecting the position of a resident in the room 1. Each of the sensors 4 outputs a detection signal which is produced by receiving infrared rays emitted from an infrared emitter disposed in a portable transreceiver 100 that is carried as required by each of the residents, and that will be described later with reference to FIG. 2. The output detection signal is supplied to a controller 6 which is disposed in the house.

Plural sensors 7 are embedded at predetermined intervals in the floor of the room 1. The sensors 7 are pressure sensors for detecting the position of a resident in the room 1. Each of the sensors 7 outputs a detection signal which is produced by sensing the pressure due to the weight of a resident, and supplies the output detection signal to the controller 6. The controller 6 has coordinate data corresponding to the positions of the sensors 4 and 7 in the room 1, and, when the detection signals are supplied from the sensors, detects the position of the resident in the room 1 on the basis of the coordinate data of the sensors.

Plural transreceivers 5 are disposed so as to respectively correspond to the sensors 4 in the room 1. The transreceivers 5 receive a signal transmitted from the portable transreceiver 100 which is carried by the resident, and which will be described later, and then supply the received signal to the controller 6. Furthermore, the transreceivers 5 transmit signals (a warning signal, etc.) which are sent as required from the controller 6.

As required, each of the residents can carry the portable transreceiver 100. The portable transreceiver 100 transmits information relating to the physical condition of the resident carrying the transreceiver, and also to the position of the resident in the house. For example, the transreceiver may be incorporated into a hearing aid so that a person who has difficulty in hearing can easily carry the transreceiver.

Figure 2:
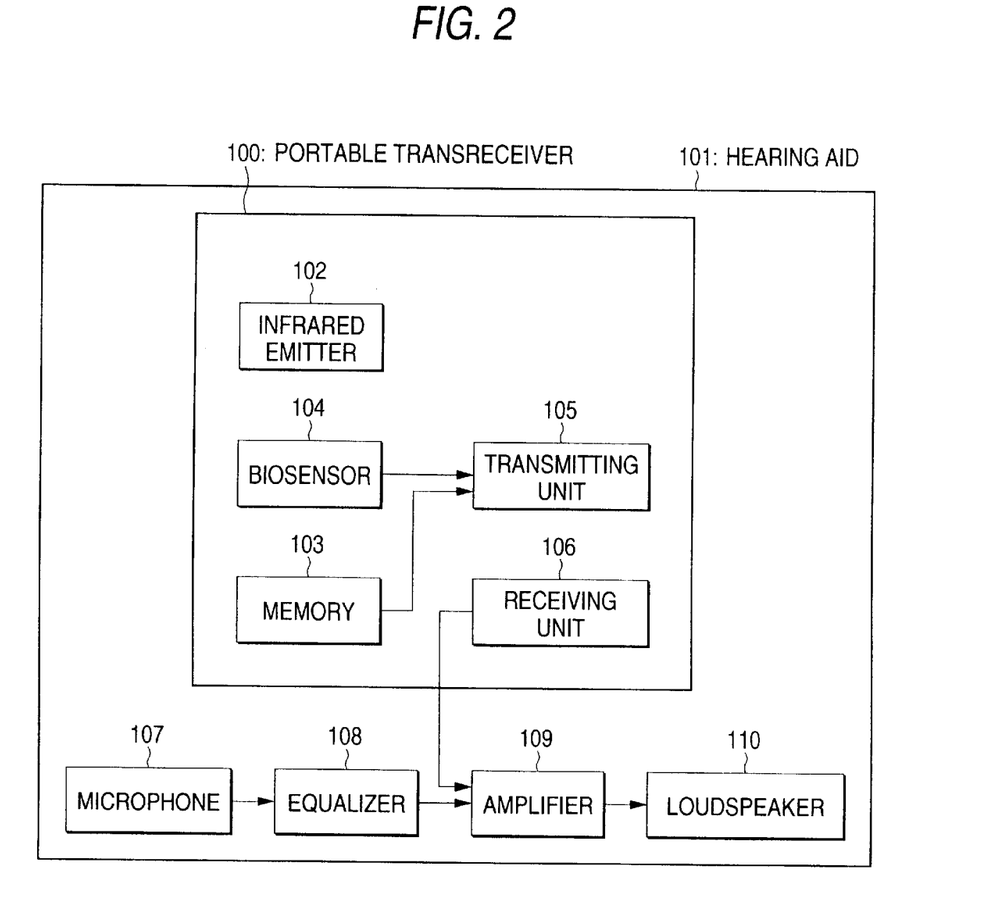
FIG. 2 is a view showing a portable transreceiver which is incorporated into a hearing aid.

FIG. 2 is a view showing the portable transreceiver 100 which is incorporated into a hearing aid 101. The portable transreceiver 100 comprises: an infrared emitter 102 which emits infrared rays; a memory 103 in which identification data for identifying the resident carrying the portable transreceiver 100 are preset and stored; a biosensor 104 which detects in sequence the pulse, the heartbeat, the blood pressure, the brain waves, the respiration rate, the body temperature, the perspiration, and the like of the resident carrying the hearing aid; a transmitting unit 105 which transmits an identification signal relating to the identification data of the memory 103, and a sensor output of the biosensor 104; and a receiving unit 106 which receives signals transmitted from the sensors 4.

The hearing aid 101 is configured so that the sound quality of environmental sound picked up by an incorporated microphone 107 is corrected by an equalizer 108 disposed in accordance with the acoustic characteristics of the ears of the person who has difficulty in hearing and carries the hearing aid, and the sound is then amplified by an amplifier 109 and acoustically reproduced by a dedicated loudspeaker 110, thereby correcting the acoustic sense of the person carrying hearing aid. The portable transreceiver 100 is incorporated into the thus configured hearing aid 101, and an output of the receiving unit 106 is supplied to the amplifier 109. According to this configuration, when the controller 6 supplies a signal such as a warning signal to the transreceivers 5 and controls them so as to transmit the signal, the signal can be received by the receiving unit 106, and hence the resident carrying the hearing aid 101 can listen to the signal through the loudspeaker 110 of the hearing aid 101.

By contrast, in the room 2, a loudspeaker 3 is disposed at a predetermined place, and a transreceiver 5 is disposed in proximity to the loudspeaker 3. In the same manner as the room 1, the transreceiver 5 receives the signal transmitted from the portable transreceiver 100 carried by a resident, and then supplies the signal to the controller 6. On the basis of the signals supplied from the transreceivers 5 of the rooms, the controller 6 obtains information (such as the vital information and the identification information of each resident) relating to the residents respectively carrying the portable transreceivers 100, and accumulates the information into a database 8.

In the database 8, the vital information of the residents, and external data such as data relating to the date, the time, and the weather when the vital information is detected are accumulated so as to correspond to the identification data. From these data, for example, the vital information in a normal state of each resident depending on the date, the time, and the weather is learned and accumulated. According to this configuration, the controller 6 receives the vital information and the identification data of a resident which are sequentially transmitted from the portable transreceiver 100 carried by the resident, via the transreceivers 5, compares the received vital information with the vital information in a normal state of the resident, and adequately conducts a switching operation of a switch 9 in accordance with the result of the comparison.

The switch 9 can independently select and switch over plural audio signal sources which are to be reproduced from the speaker of the corresponding room. The audio signal sources include a common audio signal source 10 for PA, such as a BGM or a public address which is to be listened to by the residents, a warning signal source 11 for informing an abnormality of the physical condition or an emergent state of each resident, and an individual audio signal source 12 consisting of several kinds of audio signal sources which respectively supply favorites of the residents (for example, music pieces selected by the residents, music pieces of various genres such as a popular ballad, jazz, pop, a music piece of radio broadcasting, channels of a TV, channels of a CATV, and channels of satellite broadcasting). These audio signal sources can be independently supplied.

The switch 9 is configured so that the audio signal source selected for each room is supplied also to the controller 6. The controller 6 supplies transmission signals corresponding to audio signals which are selected for the rooms, to the transreceivers 5 of the rooms, respectively. The transreceivers 5 of the rooms transmit the transmission signals. Therefore, each resident carrying the hearing aid 101 can receive the signal by means of the receiving unit 106 of the corresponding portable transreceiver 100, with the result that the resident can listen directly also from the loudspeaker 110 of the hearing aid 101, the sound which is reproduced from the corresponding loudspeaker 3.

The portable transreceiver 100 further comprises an emergency button which is not shown. When a resident carrying the transreceiver feels a failure in his physical condition, the resident presses the button, so that an emergency signal indicative of the illness of the resident is transmitted together with the identification signal and the sensor output, from the transmitting unit 105 to the transreceiver 5. The transreceiver 5 receives the signals and then supplies them to the controller 6.

The controller 6 quantitatively calculates the living condition such as the positions, the movement, and the number of residents in the room 1, by means of the sensors 4 and 7 which are disposed in the room 1 as described above. On the basis of the result of the calculation, reproduced sounds which are to be respectively emitted from the loudspeakers 3 are independently controlled at the positions of the residents, by using an audio signal processing unit 13 which will be described later, so that the residents can listen to the sounds in a predetermined level (acoustic power-frequency characteristics) range.

For each of the rooms, the controller 6 normally selects the common audio signal source 10. When a resident carrying the portable transreceiver 100 enters the room 2, the controller 6 receives the vital information and the identification data of the resident, via the transreceiver 5 of the room 2, and compares the received vital information with the vital information in a normal state of the resident. If the physical condition of a resident is not abnormal (i.e., the current vital information coincides with that in a normal state), a normal audio signal source is operative (the common audio signal source 10 or the individual audio signal sources 12) which corresponds to the current physical condition. If the physical condition of the resident does not coincide with that in a normal state, the warning signal source 11 is selected for all the rooms, and the warning signal and various kinds of information relating to the resident a (the vital information, the name, the address, data registered in an external institution, and the like) are controlled so as to be communicated to the resident and transmitted to an external medical institution, a physician in charge, a security company, an emergency center, and the like via communicating means which is not shown, such as a telephone line, or a wire or wireless apparatus.

Also when the above-mentioned emergency signal is supplied from the transreceiver 5, the controller 6 controls the switch 9 such that the warning signal source 11 is selected for the rooms. At this time, the identification data and the vital information of the resident are input to the controller 6. Therefore, an audio signal which is obtained by converting the name of the resident and the vital information at the timing of reception of the emergency signal with a predetermined conversion algorithm may be supplied as the warning signal to the audio signal processing units 13.

The audio signal sources which are switched over by the switch 9 and selected to the rooms in this way are acoustically reproduced as music or a warning address informing an abnormality of the resident, from the loudspeakers 3 of the rooms via the audio signal processing units 13 and amplifiers 14 which are disposed so as to respectively correspond to the rooms.

In accordance with the kind of the selected audio signal source, the living condition of the residents obtained by the sensors 4 and 7, the identification data sent from the transreceiver 5 and the vital information of the resident corresponding to the identification data, the controller 6 controls the transreceivers 5 and the audio signal processing units 13 so as to adequately adjust the sound quality (tone) and the sound volume (gain) of the selected audio signal source and set them for each of the loudspeakers 3. It is a matter of course that, in the case of a warning address, the volume is adjusted to a higher level at which high clearness is attained.

With respect to each of the residents carrying the portable transreceiver 100, the controller 6 selects the switch 9 and controls the transreceiver 5 and the audio signal processing units 13 in accordance with the physical condition of the resident, and the movement of the resident through the rooms. Therefore, it is possible to conduct sound reproduction for each resident in accordance with the physical condition of the resident. When the physical condition of any one of the residents is not normal, furthermore, a warning can be rapidly given to the resident, the other residents, an external medical institution, a physician in charge, a security company, an emergency center, and the like. Consequently, the residents, the external medical institution, the physician in charge, the security company, the emergency center, and the like can know the resident whose physical condition becomes worse, before the resident enters a critical state.

The audio apparatus is configured as described above. During the daily life of each resident, therefore, the resident in any one of the rooms can thoroughly enjoy favorite music comfortably and at ease, without paying attention to his physical condition.

Next, the control operation conducted by the controller 6 of the audio apparatus will be specifically described. The control operation of the controller 6 conducted in the case where the audio apparatus is disposed in a house where plural residents (including a resident A carrying the hearing aid 101) live together will be described with respect to the ordinary motion of resident A through the dwelling.

When the resident A is alone at a predetermined still position in a living room (the room 1 shown in FIG. 1), the sensors 4 respectively disposed at the predetermined positions of the room 1 receive infrared rays emitted from the infrared emitter 102 of the portable transreceiver 100 of the hearing aid 101 carried by the resident A, and the controller 6 estimates the current position of the resident A on the basis of the received light levels of the sensors 4.

The sensors 7 sense the pressure due to the weight of the resident, and supply the detection signals to the controller 6. Therefore, the controller 6 can estimate the current position of the resident A also on the basis of the detection signals. In this case, the sensors 7 may judge the number of residents in the room 1 on the basis of the detection outputs of the pressure sensors disposed in the vicinity of an entrance of the room 1, or on the basis of the distribution of the detection outputs of all the pressure sensors disposed at various positions in the room 1.

The above-mentioned sensors can conduct not only estimation of the current still position of the resident, but also detection of various active states by methods which will be described later.

A. Method of detecting the active state of a person by Means of the sensors disposed in the room 1.
  (1) Case where it is to be judged whether a single person or plural persons are in the room.
     a. Case where, from the outputs of the sensors 4 and 7 in the room, it is estimated that one or more persons exist in the room, and regions activating sensor outputs are separated that is, sensor outputs are activated in more than one location in a single room.
     b. Case where, from the outputs of the sensors 4 and 7 in the room, it is estimated that one or more persons exist in the room, and regions activating sensor outputs are larger than a predetermined area that is, sensors indicate the presence of something larger and/or heavier than any single person in the database 8.

In both cases a and b, it is judged that there exist persons the number of which is larger at least than that of the separated regions that are recognized. When one recognized region has a preset area corresponding to a single person, an estimated weight of the person is calculated from the output of the corresponding sensor 7, to judge whether the person is an adult or a child. In the case where the weight of one region is greater than that of one average person and the region has an area which is larger than the area corresponding to a single person, it is judged that plural persons are crowding.
     c. Case where, from the outputs of the sensors 4 and 7 in the room, it is estimated that one or more persons exist in the room, and estimated person's positions are changed at a frequency which is higher than a predetermined value. In this case, it cannot be considered that one person walks about, and hence it is judged that plural persons exist.

(2) Case where it is to be judged whether a person in the room is still or moving.
  a. Depending on whether the changing amount and rate (or the changing period) of a vertical force applied to the corresponding sensor 7 is within a predetermined range or not, it is judged whether the person is moving or not.
  b. Depending on whether the moving rate of person's positions estimated from the outputs of the sensors 4 and 7 in the room is within a predetermined range or not, it is judged whether the person is moving or not.
  c. For example, a detection output of sound pick-up means such as a microphone which is separately disposed in the room 1 is simultaneously supplied to the controller 6. If it is judged that the detection output contains a signal indicative of a feature (variation of the frequency spectrum or the sound pressure level, or the like) of a walking person, it is judged that there is a moving person.

(3) Case where it is to be judged that a person in the room is conducting work of some kind.
  a. If a movement of a person is detected within a predetermined time period and at a frequency which is higher than a predetermined value, it is judged that work of some kind is conducted.
  b. Case where a tool such as a cooking tool or a cleaning tool which is to be actively used by a person is currently used, and there is no information indicative of an abnormality of the tool.
  When a tool such as a cooking tool or a cleaning tool is an electronic apparatus, for example, the controller 6 electrically detects the start or end of the operation of such a tool. Alternatively, a detection output of sound pick-up means such as a microphone which is separately disposed in the room 1 may be simultaneously supplied to the controller 6. If it is judged that the detection output contains a signal indicative of a feature (variation of the frequency spectrum or the sound pressure level, or the like) produced when the cooking tool or the cleaning tool is used, it is judged that work of some kind (including estimated working contents) is currently conducted.
  c. A control signal associated with a switching operation of an air conditioner, an AV (Audio Visual) apparatus, or the like is supplied to the controller 6. If it is judged that the apparatus is operated by a person within a predetermined time period and at a frequency which is higher than a predetermined value (for example, a frequency which is larger than the number of switching operations in an automatic mode), it is judged that a person is operating the apparatus.
  d. For example, a detection output of sound pick-up means such as a microphone which is separately disposed in the room 1 is simultaneously supplied to the controller 6. If the detection output contains a signal indicative of variation of the frequency spectrum or the sound pressure level, or the like and having a predetermined level or higher and there is no information indicative of an abnormality, it is judged that a person is conducting work of some kind.

As described above, the sensors in the room 1 can detect the number, the current positions, and the movement of the residents by using various methods.

When the resident A is alone in the room 1, the controller 6 estimates, from the detection signals of the sensors obtained by the above-described methods, that one person is in the room 1 at present. When the transreceivers 5 respectively disposed in proximity to the sensors 4 receive the identification signal transmitted from the transmitting unit 105 of the portable transreceiver 100 of the resident A, and supply the signal to the controller 6, the controller 6 recognizes that the person is the resident A carrying the hearing aid 101, and controls the switching of the switch 9 to the room 1 which currently selects the common audio signal source 10, so that the audio signal source favored by the resident A (for example, one of the individual audio signal sources 12 which is previously selected by the resident A) is reproduced in the room 1.

Furthermore, the controller 6 controls the volume of the sound output from the loudspeakers 3 and at the current position of the resident A in the room 1, by means of the audio signal processing units 13 and the amplifiers 14 in accordance with the kind and contents of the selected audio signal source, so as to attain the sound volume, the sound quality, and the sound balance which are optimum to the current physical condition of the resident A. Specifically, the acoustic power characteristics are adjusted in accordance with the listening position in the room, the sound quality is adjusted so that the acoustic characteristics allowing the resident A to easily listen to music are attained, and, when the selected audio signal source is a signal source for a stereo or multichannel reproduction, the balance of the reproduced sound in the lateral and front and rear directions is adjusted.

In this case, the controller 6 compares the current physical condition information of the resident A which is sent from the transmitting unit 105 of the portable transreceiver 100 of the resident A and based on the sensor output of the biosensor 104, with that of the resident A in a normal state which has been learned and accumulated in the database 8. In accordance with a result of the comparison, the controller 6 controls the volume of the sound output from the loudspeakers 3 so as to comply with the current physical condition of the resident A.

The controller 6 supplies the audio signal which has been controlled as described above, to the transreceivers 5 of the room 1, and the transreceivers 5 receive the signal. Therefore, the resident A can comfortably listen to the music also from the loudspeaker 110 of the hearing aid 101 carried by the resident.

In the database 8, vital information consisting of physiological data as shown in the following examples is accumulated. However, data in a period when an abnormality is observed in the physical and mental conditions of the resident are not used in the construction of the database.

B. Vital information (physiological data) to be registered in the database 8

(1) Physiological data of the resident at rising and sleeping

Vital information (physiological indices) of the resident at rising and sleeping is measured by the biosensor 104 attached to the resident, a sensor attached to bedding, and the like, and the measured information is accumulated together with the date, the time, and the weather (obtained from a weather sensor, external weather information, etc.) in the database 8.

On the basis of the accumulated measured values, average physiological indices of the resident at rising and sleeping (i.e., the index which the resident has in a normal state), and noteworthy variations (a change of the number of the heartbeat, and the like) calculated from the physiological indices are registered in the database 8. As required, these values are calculated for each of external data (the month, the day in the week, the time, the weather, the number of persons in the room, etc.) relating to the environment of the resident at rising and sleeping. These average values registered in the database 8 are compared with the physiological indices which are measured at each rising and sleeping, and the physical condition of the resident such as the health state and the psychological state is estimated.

(2) Physiological data of the resident during action

In the case where the biosensor 104 is always attached to the body of the resident, physiological indices of the resident during action are measured. In the specification, the term action means any activity or motion which can be detected and/or estimated based on information from a sensor in the room or an apparatus used by the resident, such as cooking, evacuation, bathing, walking, or light work. From the thus measured physiological indices, in the same procedure as above-described (1) of B, average physiological indices in a normal state, and their variations during activity are calculated for each particular action such as described above, and the calculated values are registered in the database 8. As required, these values are calculated for each combination of activity of the resident and external data (the month, the day in the week, the time, the weather, the number of persons in the room, etc.) relating to the environment of the resident during action. On the basis of the registered values, in the same manner as above-described (1) of B, the physical condition of the resident such as the health state and the psychological state during action is estimated.

(3) Physiological data of the resident at rest

When the resident has finished action of some kind and takes a rest by sitting in a chair or the like, average physiological indices for each rest location, and their characteristic levels are calculated by using the biosensor 104 attached to the body of the resident or sensors disposed on the chair in which the resident sits, and the like for each external data (the month, the day in the week, the time, the weather, the number of persons in the room, etc.). The calculations correlated to the action of the resident as well as the environment immediately before the rest. The calculated values are recorded in the database 8. In the same manner as above-described (1) and (2) of B, also the values are used in the estimation of the physical condition of the resident such as the health state and the psychological state during action.

(4) Rhythm of variation of physiological data of the resident

By using the data collected in (1) to (3) of B, average variation (rhythm of variation) due to a temporal change of physiological indices of the resident is calculated, and the calculated value is registered in the database 8. Specifically, for each of periods such as a weekday, a holiday, one week, one month, and one year, characteristic amounts (the period, the amplitude, etc.) of variation due to a temporal change are calculated. If the rhythm of variation of physiological data during a certain period is largely different from the rhythm registered in the database 8, it can be estimated that the health state and the habit of life are changing substantially. When the recording is updated to the new rhythm of variation, therefore, the apparatus can be provided with the learning function.

In the database 8, external data relating to vital information, such as shown in the following examples are accumulated.

C. Vital information (external data) to be registered in the database 8

(1) Sound favored by the resident

When the resident uses a medium which produces a sound, such as a game, a CD, or broadcasting, features of the sound (the variation pattern of the level, the rhythm, the tempo, the frequency spectrum, a feature of pitch variation, etc.) are accumulated in the database 8, together with the time, the weather, and the physiological state at this timing, the action content, and actions and physiological states before and after the timing. On the basis of the accumulated data, the the audio apparatus of the present invention is able to ascertain the preferences of the resident and to select appropriate audio signal sources according to those preferences.

(2) Contents favored by the resident

When information indicative of contents (the source of the sound, the source of the voice, the title of the music piece, contents of the speech, contents of the words, etc.) supplied from a medium used by the resident is output together with the sound from the medium, contents favored by the resident are accumulated in the database 8, together with the time, the weather, and the physiological state at this timing, the action content, and actions and physiological states before and after the timing. On the basis of the accumulated data, the the audio apparatus of the present invention is able to ascertain the preferences of the resident and to select appropriate audio signal sources according to those preferences.

Next, the case where another resident newly enters the room where the resident A already exists will be described. In this case, when another resident B newly enters the room 1 as described above, the controller 6 and the sensors 4 and 7 of the room 1 estimate the current position and/or motion of the resident B in addition to those of the resident A. In this case, when the resident B carries the portable transreceiver 100, the controller 6 can detect the current physical condition of the resident B on the basis of the identification information and the vital information of the resident B supplied from the transreceiver 5.

Furthermore, the controller 6 recognizes that plural residents are in the room 1, and controls the switch 9 to be switched over so that the common audio signal source 10 directed to plural residents is reproduced from the loudspeakers 3 of the room 1, and also from the loudspeaker 110 of the hearing aid 101 into which the portable transreceiver 100 is incorporated and which is carried by each of the residents.

Furthermore, in accordance with the current positions and motion of the plural residents (the residents A and B) in the room 1, the controller 6 controls the volume of the reproduced sound of the common audio signal source 10 which is output from the loudspeakers 3, adjusts the acoustic power characteristics in accordance with the listening positions of the residents, adjusts the sound quality so that the acoustic characteristics allowing the residents to easily listen to music are attained, and, when the selected audio signal source is a signal source for a stereo or multichannel reproduction, adjusts the balance of the reproduced sound in the lateral and front and rear directions. In this case, it is not necessary to conduct the adjustments so that the optimum state is attained for the residents at the current positions. The adjustments are required only to be conducted in a well-balanced manner in accordance with the number and current positions of the residents in the room 1.

With respect to a resident carrying the hearing aid 101 into which the portable transreceiver 100 is incorporated, the controller 6 can detect the current physical condition of the resident on the basis of the identification information and the vital information of the resident which are supplied from the transreceiver 5. As required, therefore, the controller 6 can control the transreceiver 5 so as to transmit to each of the residents a signal which relates to the common audio signal source 10 and in which each resident's physical condition is individually considered. As a result, each of the residents can listen to a reproduced sound of the volume and quality which correspond to the physical condition of the resident, from the loudspeaker 110 of the hearing aid 101.

When each of the residents staying in the room 1 carries the portable transreceiver 100, the vital information of each resident detected by the sensor 4 is transmitted together with the identification information, and the controller 6 receives the information via the transreceiver 5. The received vital information is compared with the above-mentioned average physiological indices registered in the database 8. Alternatively, the rhythm of variation of the received vital information is compared with the rhythm of variation registered in the database 8. If a result of the comparison shows that the received vital information is deviated from that in a normal state, the controller 6 judges that the physical condition is not normal, and activates switch 9 so that the warning signal source 11 is reproduced from the loudspeakers .3 and the loudspeakers 110 of the hearing aids 101, whereby warning is given to the questioned resident and the other residents. Furthermore, the controller 6 reports that a sick person occurs, via a telephone line or by wireless to the external medical institution, the physician in charge, the security company, the emergency center, etc.

According to this configuration, when an abnormal state arises, for example, when the physical condition of one of the residents becomes worse, the other residents, the external medical institution, the physician in charge, the security company, the emergency center, and the like can know the resident whose physical condition is growing worse, before the state becomes serious. Consequently, they can rapidly take a countermeasure.

Next, the case where the resident A is moved into the room 2 (for example, a toilet room) will be described.

In this case, the controller 6 can estimate based on the sensors 4 and 7 that one person goes out of the room 1, and judge that the resident A is not in the room 1, based on the fact that the identification information relating to the resident A is not obtained from the transmission outputs from the portable transreceivers 100 which are supplied from the transreceivers 5 in the room 1. For the residents other than the resident A, therefore, the controller 6 conducts the above-mentioned volume control on the loudspeakers 3 (in the case where a resident carrying the hearing aid 101 into which the portable transreceiver 100 is incorporated is in the room, also on the loudspeaker 110).

In the case where there exists only one resident excluding the resident A, the controller 6 conducts the control in the following manner. When the one resident carries the portable transreceiver 100, the audio signal source which is selected for the room 1 is switched to one of the individual audio signal sources 12 which is favored by the resident. In the case where there exist plural residents excluding the resident A, the controller 6 conducts the control so that the common audio signal source 10 is reproduced. The individual audio signal is adequately set in accordance with the environment and the situation, by the process such as that described in "C. Vital information (external data) to be registered in the database 81" above.

When the resident A enters the room 2, the transreceiver 5 in the room 2 receives the transmission output from the portable transreceiver 100 carried by the resident A. Based on the identification information obtained from the transmission output, the controller 6 recognizes that the person who currently exists in the room 2 is the resident A.

The controller 6 selects one of the individual audio signal sources 12 which is favored by the resident A. In the same manner as the case of the room 1, the selected individual audio signal source is output from the loudspeaker 3 in the room 2. Also in this case, the controller 6 can obtain the vital information of the resident A together with the identification information of the resident A, and hence music favored by the resident A can be reproduced according to the physical condition.

In the case where the physical condition of the resident A is growing worse, the controller 6 diagnoses the health state of the resident A-by comparing the vital information detected from the sensors 4 as described above with the vital information, indices, rhythms, and the like which are registered in the database 8. Then, the controller 6 controls the switch 9 to be switched over so that the warning signal source is reproduced in all the rooms at a predetermined sound volume and sound quality.

As a result, warning can be given not only to the questioned resident, but also to the residents in other rooms who do not know which person is in the room 2, the external medical institution, the physician in charge, the security company, the emergency center, and the like. Consequently, the residents, the external medical institution, the physician in charge, the security company, the emergency center, and the like can know the resident whose physical condition is growing worse, before the state becomes serious.

The controller 6 receives the vital information of each resident, and also the identification information, and knows the room from which the information is transmitted. When one of the residents becomes ill and warning is to be given, therefore, an audio signal indicative of the name of the resident and the identification of the room may be output as a sound via the loudspeakers 3 in the rooms so as to inform of the abnormal resident and the room, or the name, the vital information, and the like may be visually reported by means of character data and an image to the external medical institution via a telephone line or the like. During the daily routine of each resident, therefore, the resident in any one of the rooms can thoroughly enjoy favorite music comfortably and at ease, without paying attention to his physical condition.

According to the invention which is configured as described above, the vital information detecting means detects vital information of a resident; at least vital information in a normal state of the resident is accumulated in the database; the comparing means compares the vital information in a normal state which is accumulated in the database, with the vital information detected by the vital information detecting means; if the detected vital information is information in a normal state, the normal audio signal of the audio signal generating means is selected, and, if the vital information is not information in a normal state, the warning audio signal is selected; and the audio signal producing means produces the selected audio signal to the resident. Even when the attention of the resident is focused on the normal audio signal, therefore, the signal is switched to the warning audio signal in the case of emergency. Consequently, even when a resident such as an aged person is in any room during ordinary daily routine, the person can enjoy music comfortably and at ease.

Furthermore, the position detection sensor detects the position of a resident in a room, and produces a detection signal corresponding to the detected position; and, on the basis of the detection signal, the level setting means sets the audio signal generated by the audio signal generating means, to a predetermined level, and supplies the audio signal to the loudspeakers which are respectively disposed at predetermined places in the room. Even when a resident is at any position, therefore, the resident can enjoy music at the volume and a level of sound quality which are suitable to the resident.

When a resident moves from the first room (a common living space such as a living room or a reception room) where the common audio signal is produced by the common audio signal producing means, to the second room (a private space such as a toilet room, a bathroom, or a private room), the identification signal receiving means disposed in the second room receives the identification signal from the identification signal producing means carried by the resident, and the selecting means selects an individual audio signal corresponding to the identification signal. Therefore, the resident can enjoy the selected audio signal which is selected for the resident.

In the embodiment, the sensors 4 and 7 are jointly disposed (or the microphones are additionally disposed as required) so that the number of the residents in the room 1 and their motion is detected. Alternatively, such information may be detected by using only one kind of the sensors 4 and 7.

When a MIDI device is used, the audio signal sources are not required to be individually disposed as the signal sources. MIDI data for producing audio signals and warning signals may be stored in the database, and the MIDI data may be output to the MIDI device so as to adequately generate audio signals and warning signals. In this case, the switches may be unnecessary.

The vital information of each resident which is sequentially detected by the biosensors is not required to be continuously detected and then transmitted to the controller. When the resident is in a normal state, the detection of the vital information and the transmission to the controller may be intermittently conducted. During a period such as a sleeping period when arrhythmia easily occurs, the frequency of the detection of the vital information must be high, and hence the frequencies of the detection and the transmission of the vital information may be set to be higher.

What is claimed is:

1. An audio apparatus comprising:
   vital information detecting means for detecting vital information of a resident;
   a database which is configured by information based on the vital information, and in which at least vital information in a normal state of the resident is accumulated;
   audio signal generating means for generating a normal audio signal and a warning audio signal;
   comparing means for comparing the vital information in a normal state which is accumulated in said database, with the vital information detected by said vital information detecting means;
   selecting means for, if vital information detected on the basis of a result of the comparison of said comparing means is information in a normal state, selecting the normal audio signal of said audio signal generating means, and, if the vital information is not information in a normal state, selecting the warning audio signal; and
   audio signal producing means for producing the selected audio signal to the resident.

2. The audio apparatus of claim 1, wherein
   said vital information detecting means is attached to a hearing aid.

3. The audio apparatus of claim 1, wherein, external data together with vital information are accumulated in said database, and the vital information in a normal state of the resident is set in accordance with the external data.

4. An audio apparatus comprising:
   a position detection sensor which produces a detection signal corresponding to a position of a resident in a room;
   audio signal generating means for generating an audio signal;
   loudspeakers which are respectively disposed at predetermined places in the room, and which output the audio signal from said audio signal generating means; and
   level setting means for, on the basis of the detection signal from said position detection sensor, setting the audio signal supplied to said loudspeakers to a predetermined level.

5. The audio apparatus of claim 4, wherein said position detection sensor comprises:
   light emitting means carried by the resident; and light receiving means, respectively disposed at predetermined places in the room, for receiving light from said light emitting means.

6. An audio apparatus comprising:
   identification signal producing means, carried by a resident, for producing an identification signal for identifying the resident;
   common audio signal generating means for generating a common audio signal;
   common audio signal producing means for producing the common audio signal in a first room;
   individual audio signal generating means for generating a plurality of individual audio signals corresponding to the identification signal of the resident;
   identification signal receiving means, disposed in a second room, for receiving the identification signal from said identification signal producing means;
   selecting means for, from said individual audio signal generating means, selecting an individual audio signal corresponding to the identification signal received by said identification signal receiving means; and
   individual audio signal producing means for producing the selected individual audio signal in said second room.

7. The audio apparatus of claim 6, wherein said identification signal producing means is attached to a hearing aid.

* * * * *